(12) United States Patent
Chauhan et al.

(10) Patent No.: US 7,230,113 B2
(45) Date of Patent: Jun. 12, 2007

(54) CHEMICAL COMPOSITIONS FOR AUTHENTICATABLE POLYMERS AND ARTICLES, AND AUTHENTICATION METHODS THEREOF

(75) Inventors: Yogendrasinh Chauhan, Gujarat (IN); Adil Dhalla, Maharashtra (IN); Sriramakrishna Maruvada, Evansville, IN (US); Shantaram Naik, Karnataka (IN); Vandita Pai-Paranjape, Evansville, IN (US); Kiran Puthamane, Maharashtra (IN); Meerakani Sait, Tamil Nadu (IN); Philippe Schottland, Evansville, IN (US); Ganapati Shankarling, Karnataka (IN)

(73) Assignee: General Electric Company, Schenectady, NY (US)

( * ) Notice: Subject to any disclaimer, the term of this patent is extended or adjusted under 35 U.S.C. 154(b) by 103 days.

(21) Appl. No.: 11/016,319

(22) Filed: Dec. 17, 2004

(65) Prior Publication Data

US 2006/0135658 A1 Jun. 22, 2006

(51) Int. Cl.
*C07D 235/02* (2006.01)
*C08K 5/3447* (2006.01)
(52) U.S. Cl. .................... 548/301.7; 524/89
(58) Field of Classification Search ............. 524/89; 548/301.7
See application file for complete search history.

(56) References Cited

U.S. PATENT DOCUMENTS

| | | | | |
|---|---|---|---|---|
| 3,474,109 A | * | 10/1969 | Hirata et al. ............. | 540/303 |
| 3,544,573 A | | 12/1970 | Christmann ............. | 260/256.4 |
| 4,087,409 A | | 5/1978 | Preston .................... | 260/65 |
| 6,087,510 A | | 7/2000 | Donovan et al. ......... | 548/335.1 |
| 6,099,930 A | | 8/2000 | Cyr et al. ................. | 428/64.1 |
| 6,296,911 B1 | | 10/2001 | Guillen .................... | 428/29 |
| 6,514,617 B1 | | 2/2003 | Hubbard et al. .......... | 428/412 |
| 2002/0149003 A1 | | 10/2002 | Lucht et al. .............. | 252/408.1 |

FOREIGN PATENT DOCUMENTS

| | | |
|---|---|---|
| FR | 1090115 | 3/1955 |
| JP | 1993021823 A | 1/1993 |
| WO | WO 00/14736 | 3/2000 |

OTHER PUBLICATIONS

Sek et al. Polymer (1998), 39(26), 7001-7008.*
Korshak et al. Vysokomolekulyarnye Soedineniya, Seriya A (1972), 14(1), 186-201. *CAS abstract attached.*
International Search Report; International Application No. PCT/US2005/043423; International Filing Date: Dec. 1, 2005; Date of Mailing: Jun. 8, 2006; 9 pages.

Korshak et al.; "Interaction of Aroylenebenzimidazoles with Nucleophilic Reagents"; Abstract Only; Retrieved from STN Database accession No. 1972:140644; XP002376909; 2 pages (1972).
Korshak et al.; "Polybenzimidazoles containing Benzimidazolyl Side Groups"; Abstract Only; Retrieved from STN Database accession No. 1974:464014; XP002376908; 2 pages (1974).
Korshak et al.; "Synthesis and Study of Some Bis(3-amino-4-N-phthalimido)arylenes and Bis(1,2-benzoylenebenzimidazoles)"; Abstract Only; Retrieved from STN Database accession No. 1976:74179; XP002376907; 2 pages (1976).
Korshak et al.; "Study of Thermal and Hydrolytic Stability of a Series of Heterocyclic Compounds Simulating 'Ladder' Polyheteroarylenes"; Abstract Only; Retrieved from STN Database accession No. 1977:551471; XP002376906; 1 page (1977).
Japan Publication No. JP5021823 (Application No. 1993:570131); Abstract Only; 1 page; XP002376905.
Niyazi et al.; The Chemical Polyfunctional additives for the Heterochain Polymers; Abstract Only; Retrieved from SNT Database accession No. 1996:706934; XP002376904; 2 pages (1996).

* cited by examiner

*Primary Examiner*—Kamal A. Saeed
*Assistant Examiner*—Jason M. Nolan

(57) ABSTRACT

Disclosed are compositions comprising at least one [benzo[4,5]imidazo(heterocycle)] compound, said [benzo[4,5]imidazo(heterocycle)] compound selected from the group consisting of structures I and II,

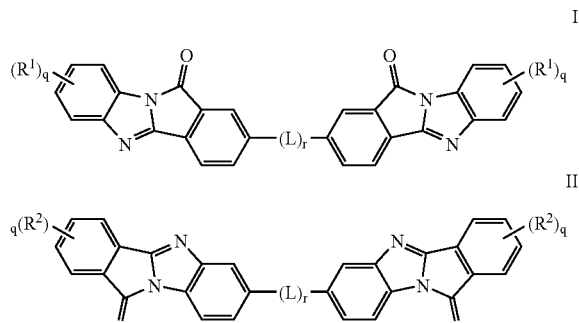

wherein $R^1$ and $R^2$ are independently selected from the group consisting of a hydrogen atom, electron withdrawing group, organic group, divalent 1,2-cycloalkylidene group, or combinations thereof; "q" is independently an integer from 1–4, L is a linking group, and "r" is independently 0 or 1; said at least one [benzo[4,5]imidazo(heterocycle)] compound being present at a concentration sufficient to cause said composition to exhibit upon exposure to an excitation radiation having a wavelength of from about 330 nanometers to about 390 nanometers, a maximum fluorescence emission wavelength of greater than or equal to about 470 nanometers; and a Stokes shift of greater than or equal to about 80 nanometers; wherein the wavelengths are measured in bisphenol A polycarbonate matrix.

38 Claims, No Drawings

CHEMICAL COMPOSITIONS FOR AUTHENTICATABLE POLYMERS AND ARTICLES, AND AUTHENTICATION METHODS THEREOF

BACKGROUND

The invention relates to chemical compositions and their use as taggants for producing authenticatable polymers and articles, and methods for authenticating these polymers and articles. The invention is useful in security applications, particularly for authenticating articles such as security documents, pharmaceutical packaging, telecom accessories, such as cellular phone covers and batteries, and data storage media, such as compact disks (CDs) and digital versatile disks (DVDs).

A major problem confronting the various makers and users of data storage media is the unauthorized reproduction or copying of information by unauthorized manufacturers, sellers and/or users. Electronics-based and software-based approaches have been used. Piracy has evolved to the point that unauthorized duplicates now contain the original electronic anti-piracy circuit, code, etc. For example, standard holograms are now easily counterfeited and no longer guarantee the authenticity of a product. Similarly, computer codes to remove anti-piracy features and enable unlimited access to the data have been developed. Regardless of the manner, piracy of data storage media deprives legitimate software and entertainment content providers and original electronic equipment manufacturers of significant revenue and profit. Numerous approaches to thwart such consumer level piracy have been developed. One such approach involves the placement of 'tags' or authentication markers in substrates used in the construction of data storage media, such as those disclosed in U.S. Pat. Nos. 6,099,930, 6,514, 617, 6,296,911, U.S. Patent Application No. 2002/0149003A1, and World Patent Application No. WO 00/14736.

There is also a need for chemical compositions that can be incorporated as taggants in polymer matrices through traditional processes such as molding, extrusion, and the like. In the case of engineering thermoplastics, such as polycarbonate, such processes often involve high temperatures, of the order of 280° C., or even higher. Under these high temperatures and residence times in the processing equipment, the chemical compositions known in the art generally tends to decompose or degrade, thereby leading to an unsatisfactory performance as an effective taggant in the finished polymer composition or molded article.

Therefore, there is a need for more effective and thermally stable chemical entitites, which can be used as authentication tags (or taggants) or combinations of taggants for use in polymers and articles, particularly those comprising engineering thermoplastics. It would also be desirable to provide methods for preparing such chemical compositions, and authenticating the polymer compositions and articles, such that genuine manufacturers, sellers, and/or users of the authenticatable polymer compositions and authenticatable articles are not adversely affected by unauthorized manufacturers.

BRIEF DESCRIPTION OF THE INVENTION

A first aspect of the disclosure is a composition comprising at least one [benzo[4,5]imidazo(heterocycle)] compound, said at least one [benzo[4,5]imidazo(heterocycle)] compound being selected from the group consisting of structures I and II;

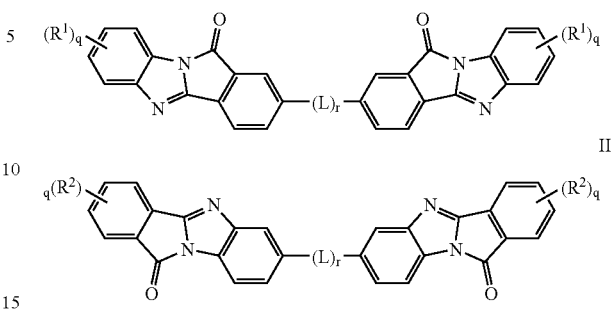

wherein $R^1$ and $R^2$ are independently selected from the group consisting of a hydrogen atom, electron withdrawing group, organic group, divalent 1,2-cycloalkylidene group, or combinations thereof; "q" is independently an integer from 1–4, L is a linking group, and "r" is independently 0 or 1; and wherein said at least one [benzo[4,5]imidazo(heterocycle)] compound is present in said composition at a concentration sufficient to cause said composition to exhibit upon exposure to an excitation radiation having a wavelength of from about 330 nanometers to about 390 nanometers, a maximum fluorescence emission wavelength of greater than or equal to about 470 nanometers; and a Stokes shift of greater than or equal to about 80 nanometers; wherein the wavelengths are measured in bisphenol A polycarbonate matrix.

A second aspect of the disclosure is a compound having a structure I,

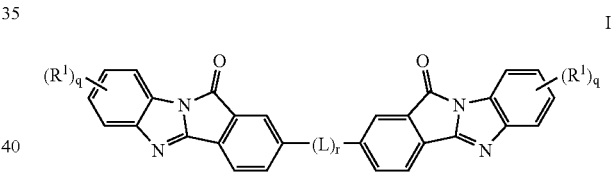

wherein $R^1$ is independently selected from the group consisting of a hydrogen atom, electron withdrawing group, organic group, divalent 1,2-cycloalkylidene group, or combinations thereof; "q" is an integer from 1–4, L is a linking group, and "r" is 0 or 1.

A fourth aspect of the disclosure is a method for authenticating that an article is an authenticatable article having a standard signal, where the authenticatable article comprises a taggant. The method comprises: irradiating a test portion of the article with ultraviolet radiation by using an optical tester comprising an ultraviolet radiation source and a photodetector, measuring a test signal emitted by the article, and authenticating that the article is an authenticatable article if the test signal matches the standard signal; wherein the taggant comprises at least one [benzo[4,5]imidazo(heterocycle)] compound, said at least one [benzo[4,5]imidazo (heterocycle)] compound being present in said taggant at a concentration sufficient to cause said taggant to exhibit upon exposure to an excitation radiation having a wavelength of from about 330 nanometers to about 390 nanometers, a maximum fluorescence emission wavelength of greater than or equal to about 470 nanometers; and a Stokes shift of greater than or equal to about 80 nanometers.

A fourth aspect of the disclosure is a method for preparing a [2,2']bis{[benzo[4,5]imidazo[2,1-a]isoindolyl]-11-one} compound. The method comprises: contacting an aromatic dianhydride having a structure III

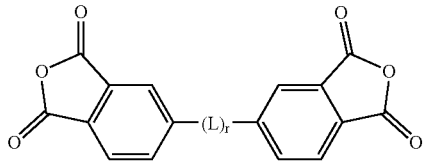

wherein L is a linking group, and "r" is 0 or 1; with an aromatic diamine having a structure IV,

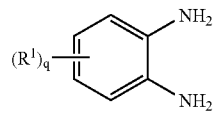

wherein $R^1$ is selected from the group consisting of a hydrogen atom, electron withdrawing group, organic group, divalent 1,2-cycloalkylidene group, or combinations thereof; and "q" is an integer from 0–4; and forming the [2,2']bis{[benzo[4,5]imidazo[2,1-a]isoindolyl]-11-one}compound having a structure I

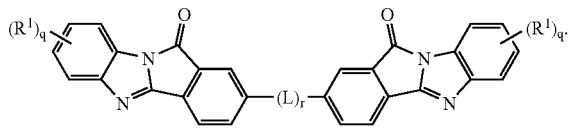

A fifth aspect of the disclosure is a polymer composition comprising a purified [7,7']bis{[benzo[4,5]imidazo[2,1-a]isoindolyl]-11-one} compound, which is prepared by a method comprising: contacting an aromatic tetraamine having a structure V;

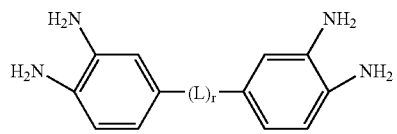

wherein "L" is a linking group, and 'r' is 0 or 1; with an aromatic monoanhydride having a structure VI,

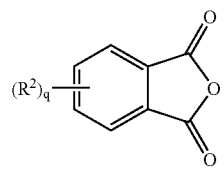

wherein $R^2$ is selected from the group consisting of a hydrogen atom, electron withdrawing group, organic group, divalent 1,2-cycloalkylidene group, or combinations thereof; and "q" is an integer from 0–4; forming a first intermediate product, treating said first intermediate product with a first solvent, isolating a second intermediate product, treating said intermediate product with a second solvent, and isolating said [7,7']bi[benzo[4,5]imidazo[2,1-a]isoindolyl]-11,11'-dione compound having a structure II:

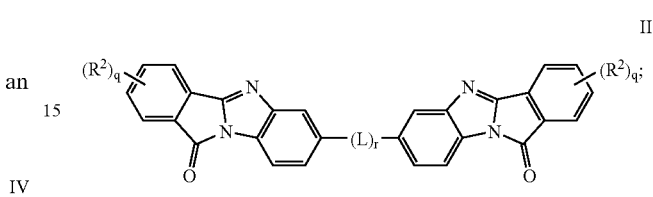

wherein said compound upon exposure to an excitation radiation having a wavelength of from about 330 nanometers to about 390 nanometers exhibits a fluorescence emission having a wavelength of from about 470 nanometers to less than 530 nanometers, and wherein the wavelengths are measured in bisphenol A polycarbonate matrix; said compound being present in a concentration sufficient to produce a composition capable of exhibiting said fluorescence emission.

Other aspects of the invention include polymer compositions and articles comprising the comprising the at least one [benzo[4,5]imidazo(heterocycle)] compound described above.

DETAILED DESCRIPTION

The present invention may be understood more readily by reference to the following detailed description of preferred embodiments of the invention and the examples included therein. In the following specification and the claims which follow, reference will be made to a number of terms which shall be defined to have the following meanings:

The singular forms "a", "an" and "the" include plural referents unless the context clearly dictates otherwise.

The term "optional" or "optionally" means that the subsequently described event or circumstance may or may not occur, and that the description includes instances where the event occurs and instances where it does not.

As used herein, the term "1,2-cycloalkylidene group", when applied to the [benzo[4,5]imidazo(heterocycle)] compounds disclosed herein, means a cycloalkylidene group having from 3 to 6 carbon atoms, which can be fused with any two vicinal aromatic ring carbon atoms of the [benzo[4,5]imidazo(heterocycle)] compound available for forming the 1,2-cycloalkylidene group. Examples of groups that can form the 1,2-cycloalkylidene group include 1,3-propylidene, 1,4-butylidene, 1,5-pentylidene, 1,6-hexylidene, and the like. Thus for example, when a 1,3-propylidene group forms a fused ring with any two vicinal aromatic carbon atoms available for bonding, a 1,2-cyclopentylidene ring results.

As used herein the term "aliphatic group" refers to a radical having a valence of at least one comprising a linear or branched array of atoms, which is not cyclic. Examples of aliphatic groups include methyl, methylene, ethyl, ethylene, hexyl, hexamethylene, and the like. As used herein the term "cycloaliphatic group" excludes the "1,2-cycloalkylidene group" (described above) and refers to a group having a valence of at least one and comprising an array of atoms which is cyclic but which is not aromatic. Examples of cycloaliphatic groups include cyclopropyl, cyclopentyl cyclohexyl, and the like. As used herein the term "aromatic group" refers to a group having a valence of at least one comprising at least one aromatic group. Aromatic groups comprising one or more heteroatoms, such as oxygen, sulfur, and nitrogen are also defined herein as "aromatic groups". Examples of aromatic radicals include phenyl, pyridyl, furanyl, thienyl, naphthyl, anthracenyl, and the like.

As defined herein, the term "halogen group" refers to the monoatomic halogen atoms Cl, Br, F, and I.

As used herein, the term "electron withdrawing group" refers to a halogen group or any carbon-bonded group having an electronegative center bonded to an aromatic ring carbon atom. The electronegative center of the electron withdrawing group can comprise a carbon atom, a nitrogen atom, or a sulfur atom. Non-limiting examples of electron withdrawing groups includes trifluoromethyl, carbonyl-containing groups, such as ester groups, carboxylic acid group, acetyl, benzoyl, propanoyl, butanoyl, pentanoyl, methoxycarbonyl, ethoxycarbonyl, and acetoacetyl; nitro, chloro, bromo, iodo, fluoro, alkylsulfonyl, arylsulfonyl, and the like.

As used herein, the term "absorption cut-off wavelength", as applied to any of the compounds used for authentication technology refers to the highest UV-visible wavelength in the UV-visible spectrum of the compound corresponding to 5% of the maximum absorption intensity, the compound being present as a solution in a suitable solvent.

As used herein, the term "maximum fluorescence emission", refers to the wavelength at maximum fluorescence intensity for a [benzo[4,5]imidazo(heterocycle)] compound when it is present in a polymer matrix, such as for example, a polycarbonate polymer matrix.

As used herein, the term "Stokes shift" in one embodiment is defined as the wavelength difference between the wavelength at maximum absorption and the wavelength at maximum emission intensity. In another embodiment, "Stokes shift" is defined as the difference between the maximum fluorescence emission wavelength and the excitation wavelength, particularly when the difference between the maximum absorption wavelength and the maximum excitation wavelength is less than or equal to about 20 nanometers.

As used herein, the term "organic group" refers collectively to aliphatic, cycloaliphatic, and aromatic groups. Suitable organic groups exclude the electron withdrawing groups as defined above in this disclosure. The organic group may further comprise one or more heteroatoms.

As used herein, the terms, "radiation responsive compound" and "fluorophore" are used interchangeably.

One aspect of the disclosure is a composition comprising at least one [benzo[4,5]imidazo(heterocycle)] compound selected from the group consisting of structures I and II, as previously described. A suitable bisphenol A (BPA) polycarbonate matrix is exemplified by HF1110R, which is produced by GE Plastics, and having a melt flow rate of 25. The wavelength measurements are carried out on 1 millimeter thick molded chips of BPA polycarbonate samples having a 0.005 weight percent concentration of the [benzo[4,5]imidazo(heterocycle)] compound. The measurements (whether it is fluorescence or absorption spectroscopy) are baseline corrected, that is, they are corrected for the absorption or emission of the base resin. The BPA resins used generally are clear, transparent resins with a light transmission of about 89% (as measured using ASTM D1003 test method). The BPA polycarbonate can be prepared by interfacial polymerization of BPA with a carbonyl halide (eg., phosgene), or melt polymerization of BPA with a diaryl carbonate (eg., diphenyl carbonate).

The maximum fluorescence emission wavelength and Stokes shift may be affected by the nature of the solvent (termed "solvatochromism"). Further, the fluorescence emission and Stokes shift may be affected by the nature of the intermolecular and intramolecular interactions between the fluorophore molecules in a solution or solid phase (e.g., in a solid polymer matrix). Several methods can be envisaged for determining the maximum fluorescence emission wavelength and Stokes shift. One method involves the determination in the actual article (i.e. resin matrix) using fluorescence spectroscopy (or fluorimetry). Fluorimetry at set excitation wavelengths between 330 nm and 390 nm can reveal the location of the maximum fluorescence emission. By locking the detector at a wavelength corresponding to the maximum fluorescence emission, generation of the spectrum will allow the determination of the maximum wavelength (typically in the 300 to 390 nm range) at which fluorescence excitation is maximum. The Stokes shift in this case would then be defined as the difference between the maximum fluorescence emission wavelength and the maximum excitation wavelength. If the test sample does not contain additional colorant, then the determination of maximum absorption in the excitation range may be done using simple absorption spectroscopy. Alternatively, the properties of the fluorophore may be specified in a solvent (e.g. dichloromethane). In one embodiment, the authenticatable article or polymer sample may be dissolved using a solvent (possibly the same as the one used to determine the fluorescence characteristics of the fluorophore) and the fluorophore present in the authenticatable article may be isolated by chromatography techniques, such as HPLC. If needed, the solvent may be evaporated and the fluorophore dissolved in a suitable solvent to measure specifically the fluorescence emission and optical absorption in order to determine Stokes shift and maximum fluorescence emission.

In one embodiment, the composition may comprise impurities and/or contaminants in addition to the at least one compound. It will be appreciated that such impurities and/or contaminants may affect the maximum fluorescence emission wavelength and Stokes shift of the composition if present in too large a concentration. Accordingly, in one embodiment, such impurities and/or contaminants will be removed via purification processes as discussed herein. In one exemplary embodiment, the maximum fluorescence emission wavelength and Stokes shift of the composition is substantially the same as the maximum fluorescence emission wavelength and Stokes shift of the at least one compound. That is, in one exemplary embodiment, the amount of any impurities and/or contaminants in the composition will be such that they do not affect the maximum fluorescence emission wavelength or Stokes shift of the composition. In another embodiment, the composition has an absorption cut-off wavelength in the UV-visible spectrum of less than or equal to about 420 nanometers. Such a composition may be referred to as a 'purified' composition.

A wide variety of structural variations in the [benzo[4,5]imidazo(heterocycle)] compounds represented by structures I and II are possible for use as taggant compositions. The linking group "L" can be any di, or higher valent group that can link the two tetracyclic fragments present in each of structures I and II. For example, the linking group can be any carbon-based group, such as a divalent aliphatic, aromatic, or cycloaliphatic group; a heteroatom-based linking group, such as for example, a silicon-based group, a sulfur-based group, such as for example, sulfide, sulfoxy, or sulfone group; a nitrogen-based group, a carbonyl group, and the like.

Examples of carbon-based linking groups include divalent groups having the formula $CR^3R^4$, wherein $R^3$ and $R^4$ are independently of each other selected from the group consisting of aliphatic, cycloaliphatic, and aromatic groups, optionally substituted with one or more heteroatoms such as nitrogen, oxygen, and sulfur. Non-limiting examples of aliphatic groups include $C_1$–$C_{20}$ aliphatic groups, such as methyl, ethyl, n-propyl, isopropyl, tertiary-butyl, neopentyl, isohexyl, isooctyl, cyclohexylmethyl, cycloheptylmethyl, cyclopentylmethyl, and the like. Non-limiting examples of cycloaliphatic groups include $C_3$–$C_{12}$ cyclic groups, such as cyclohexyl, cyclopentyl, cyclopropyl, cyclobutyl, cycloheptyl, cyclooctyl, and the like. Non-limiting examples of aromatic groups include phenyl, naphthyl, and the like.

Examples of silicon-based linking groups include diaklylsilyl, dialkoxysilyl, alkylalkoxylsilyl, groups, and the like. Other examples of silicon-based groups include structures comprising two or more organosilicon groups, in which the two terminal groups may comprise at least one organosilicon group that can link to the tetracyclic moieties of structures I or II. Examples of nitrogen-based groups include a secondary amino group (NH), or a tertiary nitrogen group, such as an N-alkylamino, N-arylamino, or an N-cycloalkylamino group. Suitable sulfur-based groups include any group comprising one or more sulfur atoms, wherein at least one sulfur atom links one or both tetracyclic moieties. Some examples of sulfur-based groups include sulfide group, sulfoxide group, and sulfone group.

In an embodiment, the linking group "L" is independently selected from the group consisting of C=O, S, O, $SO_2$, and $CR^3R^4$, wherein $R^3$ and $R^4$ are independently selected from the group consisting of a hydrogen atom, an aliphatic group, an aromatic group, a cycloaliphatic group, and combinations thereof; and "r" is 1.

In an embodiment, the compounds of structure (I) are preferably such that q has a value of 1. Such compounds can be prepared by reacting an ortho-phenylene diamine of structure IV, wherein "q" is 1; with a dianhydride of structure III. Ortho-phenylene diamine itself is a preferred material since it is readily available commercially. Reaction of ortho phenylene diamine with dianhydride II provides [benzo[4,5]imidazo(heterocycle)] compounds of structure I in which $R^1$ is a hydrogen atom, "q" is 1; and "r" is 1. When two different ortho-phenylene diamines having different $R^1$ and "q" values are used, a mixture of [benzo[4,5]imidazo (heterocycle)] compounds having all possible combinations of $R^1$ and "q" values can be obtained.

In another embodiment, "q" is 1, "r" is 1, and "L" is a linking group selected from the group consisting of O, C=O, S, $SO_2$, and $CR^3R^4$, wherein $R^3$ and $R^4$ are independently selected from the group consisting of a hydrogen atom, an aliphatic group, an aromatic group, a cycloaliphatic group, and combinations thereof. The requisite dianhydrides for preparing compounds of this type are shown below in structures VII–XI, wherein $R^3$ and $R^4$ are as described previously.

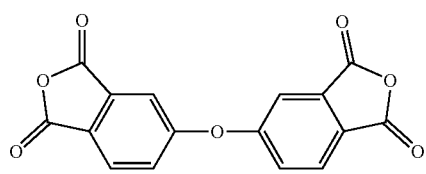

VII

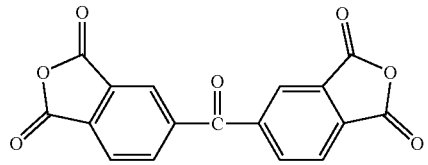

VIII

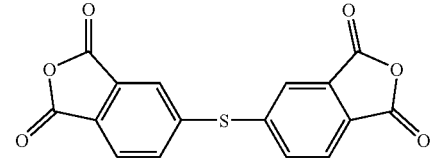

IX

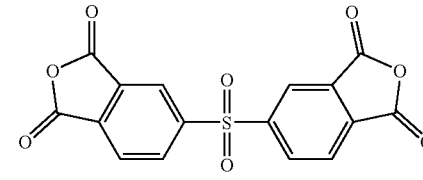

X

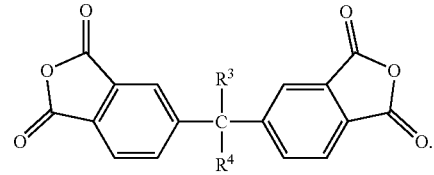

XI

For example, oxydiphthalic anhydride (structure VII), which is a bis(3,4-anhydride), can be readily prepared by methods known in the art. Another example of a suitable dianhydride is the compound XI, wherein $R^3$ and $R^4$ are methyl groups.

Other regioisomeric forms of the dianhydrides described above, such as for example the bis(2,3 anhydride) form of oxydiphthalic anhydride can also be used. Mixtures comprising the bis(3,4-anhydride) and bis(2,3-anhydride) forms can also be used in a condensation reaction with an ortho-phenylene diamine of structure III to form a mixture comprising the corresponding [benzo[4,5]imidazo(heterocycle)] compounds of structure I and their isomeric forms.

In other embodiments, suitable dianhydrides also include those in which the linker "L" comprises structural units derived from a dihydroxy aromatic compound, as shown in structure XII,

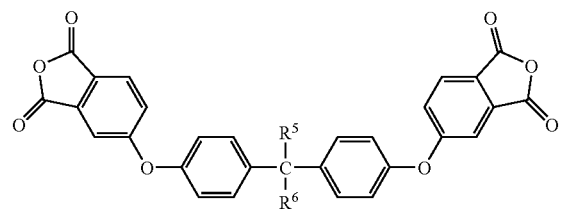

XII wherein $R^5$ and $R^6$ are independently aliphatic groups, aromatic groups, or combinations thereof; or $R^5$ and $R^6$ taken together form part of a cyclic ring having from 5 to 12 carbon atoms.

In a particular embodiment, the dianhydride of structure III has a structure such that "r" is 0, that is, 1,1'-biphenyl-3,4,3'4'-dianhydride (hereinafter referred to as BPDA). BPDA can be condensed with ortho-phenylene diamines of structure IV to produce a host of [benzo[4,5]imidazo(isoindolyl)] compounds. In a particular embodiment, when 4-benzoyl-ortho-phenylene diamine is reacted with BPDA, the product has a structure XIII, which also shows the numbering system in accordance with the Hantzsch-Widman rules of nomenclature.

XIII

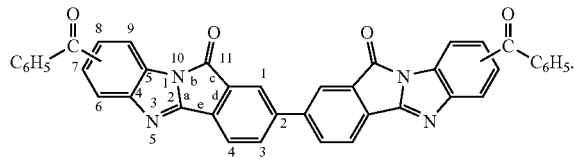

For example, the compound having structure XIV,

XIV

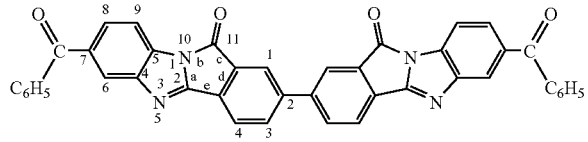

which is an isomer of structure of XIII, can be properly named as 7,7'-dibenzoyl-[2,2']bi[benzo[4,5]imidazo[2,1-a]isoindolyl]-11,11'-dione.

Compounds of structure I are very useful in authentication technology. These compounds have a unique combination of key spectral properties, such as a low visible color, an ability to absorb electromagnetic radiation, and photons in particular, such as ultraviolet radiation (for example, from a UV lamp, light emitting diode or laser) and emit a fluorescence radiation in the visible region such that they display long Stokes shift of greater than or equal to 80 nanometers in an embodiment, greater than or equal to 100 nanometers in another embodiment, and greater than or equal to 120 nanometers in yet another embodiment. Further, these compounds have an absorption cut-off wavelength in the UV-visible spectrum of less than or equal to about 420 nanometers. These properties make them excellent taggant candidates for producing authenticatable polymer compositions and authenticatable articles thereof. In an exemplary embodiment, suitable compounds of structure I have an absorption cut-off wavelength in the UV-visible spectrum of less than or equal to about 420 nanometers, a maximum fluorescence emission wavelength of greater than or equal to about 470 nanometers, and a Stokes shift of greater than or equal to about 100 nanometers.

Suitable bis[benzo[4,5]imidazo(heterocycle)] compounds of structure II include those in which "q" preferably has a value of 1. Compounds of this type, also called as [7,7']bis{[benzo[4,5]imidazo[2,1-a]isoindolyl]-11-one} compounds, can be prepared by condensing two moles of a substituted or unsubstituted phthalic anhydride with one mole of the tetraamine having structure V,

V

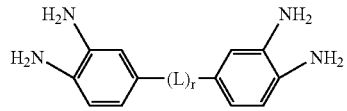

wherein "L" is a linking group as described previously, and 'r' is 0 or 1. When "r" is 0, the compound of structure V becomes 3,4,3',4'-tetraamino-1,1'-biphenyl, one mole of which can be condensed with 2 moles of phthalic anhydride to provide a product having structure II, wherein "r" is 0, "q" is 1, and $R^2$ is a hydrogen atom.

Suitable phthalic anhydrides also include the halogenated phthalic anhydrides, such as chlorinated phthalic anhydrides. Specific examples of chlorinated phthalic anhydrides include mono-, di-, tri-, and tetra-chlorophthalic anhydrides. These compounds are readily available either as mixture of isomers, or as specific isomers by chlorination of phthalic anhydride using methods known in the art. The chlorinated phthalic anhydrides can be reacted with a suitable tetraamine of structure V to furnish a wide variety of bis[benzo[4,5]imidazo(heterocycle)] compounds of structure II in which $R^2$ is a chlorine atom, "q" is 1–4, and "r" is 0 or 1.

In a specific embodiment, when the tetraamino compound of structure V is 3,4,3',4'-tetraamino-1,1'-biphenyl (that is "r"=0), and it is reacted with phthalic anhydride, the resulting product (also called as [7,7']bi[benzo[4,5]imidazo[2,1-a]isoindolyl]-11,11'-dione) has structure II in which $R^2$ is hydrogen atom, and "q" is 4.

The electron withdrawing group in structures I and II are independently selected from the group consisting of an ester group, a carboxylic acid group, a ketone group, a halogen group, a nitro group, a cyano group, a trifluoromethyl group, a sulfone group, and combinations thereof. In an embodiment, the electron withdrawing group is a ketone group having a formula $COR^7$, wherein $R^7$ is selected from the group consisting of a $C_1$–$C_{12}$ aliphatic, cycloaliphatic, or aromatic group. In another embodiment, the electron withdrawing group is an ester group having a formula $COOR^8$, wherein $R^8$ is selected from the group consisting of a $C_1$–$C_{12}$ aliphatic, cycloaliphatic, or aromatic group.

In a particular embodiment, the taggant composition comprises at least one member selected from the group consisting of structures XIII and XV

XIII

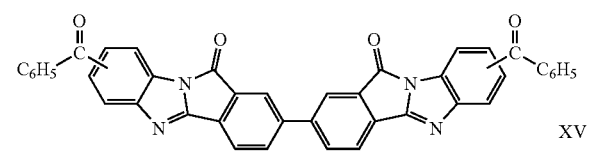

XV

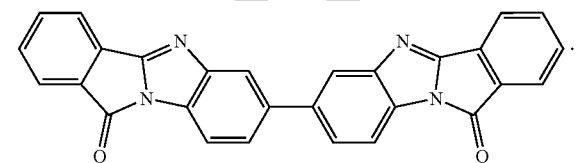

As described previously, the taggant compositions of structure I (also generally referred to as [2,2']bis{[benzo[4,5]imidazo[2,1-a]isoindolyl]-11-one} compounds) can be prepared by reacting dianhydrides of structure III with an ortho-phenylene diamine of structure IV. The method generally comprises heating one mole of the dianhydride and 2 moles of the ortho-phenylene diamine in a solvent, said solvent being selected from the group consisting of an aliphatic carboxylic acid, an aromatic monohydroxy compound, a cycloaliphatic alcohol, halogenated and non-halogenated liquid aromatic hydrocarbons, N,N-dialkylamides, cyclic N-alkyl amides, and mixtures of the foregoing solvents. A slight excess (typically between about 5–20 mole percent) of the ortho-phenylene diamine over the dianhydride is often beneficial in giving relatively higher yields of the desired product. The reaction progress can be followed by analytical methods, such as liquid chromatography. The reaction product is isolated by filtration of the reaction mixture. The reaction product can either be used as such for further applications, or if desired, based on the type of application, it can be further purified. Generally, for applications as a taggant in authentication technology, it is desirable to purify the reaction product since it will help lower the visible color of the material. Purification may also lead to a relatively higher concentration of the desired purified product in the final isolated product, which may lead to a sharper, more defined fluorescence emission signal upon excitation with a suitable excitation radiation (for example UV radiation). In an embodiment, purification can be accomplished by treating the [2,2']bis{[benzo[4,5]imidazo [2,1-a]isoindolyl]-11-one} reaction product with a first solvent, isolating an intermediate [2,2']bi[benzo[4,5]imidazo[2,1-a]isoindolyl]-11,11'-dione, treating the intermediate purified [2,2']bi[benzo[4,5]imidazo[2,1-a]isoindolyl]-11,11'-dione with a second solvent, and isolating a purified [2,2']bi[benzo[4,5]imidazo[2,1-a]isoindolyl]-11,11'-dione. Therefore, in an embodiment, the purification step removes impurities, which are soluble in the first solvent and the second solvent. The presence of these impurities and the removal of these impurities can be conveniently followed by techniques such as high pressure liquid chromatography (HPLC). The impurities may comprise, among other chemical species, partly reacted intermediates formed during the course of the cyclization reaction to form the desired polycyclic heterocycle compound. These intermediates may not possess the right extent, or the right type of conjugation to exhibit the desired fluorescence emission in the green region of the visible spectrum and the long Stokes shift of greater than or equal to 80 nanometers. Thus, purification helps in removal of such impurities and improves the performance of the isolated product as an authentication taggant in polymer compositions and articles made of such polymer compositions.

In an embodiment, the first solvent and the second solvent comprises at least one member selected from the group consisting of an aromatic hydrocarbon and a partially hydrogenated aromatic hydrocarbon. Dihydronaphthalene is a preferred first solvent. A preferred second solvent is one that is selected from the group consisting of toluene, xylenes, mesitylene, and mixtures thereof. A very common impurity in reactions between anhydrides and amines are generally the raw materials themselves and some residual solvent. The impurity that is the most likely to be present at a higher loading is probably the anhydride. At very high purity, traces of solvent can be found, especially if the boiling point of the solvent is very high. Removal of high boiling solvents requires drying under high vacuum for a prolonged period of time.

Compounds having structure II can be prepared by reacting a tetraamino diaryl compound with a aromatic monoanhydride, as described previously. These compounds, sometimes also referred to as [7,7']bis{[benzo[4,5]imidazo[2,1-a]isoindolyl]-11-one} compounds are generally prepared by heating together one mole of the tetraamino diaryl compound with two moles of an aromatic monoanhydride. A slight excess (between about 5–10 percent molar excess) of the monoanhydride is often beneficial in giving relatively higher yields of the desired product. As in the case of compounds of structure I, further purification of the reaction product is frequently necessary in order to obtain a product having lower visible color, relative to the color of the reaction product. Purification may also lead to a relatively higher concentration of the desired purified product in the final isolated product, which may lead to a sharper, more defined fluorescence emission signal upon excitation with a suitable excitation radiation (example UV radiation). Purification is accomplished by treating the [7,7']bis{[benzo[4,5]imidazo[2,1-a]isoindolyl]-11-one} reaction product with a first solvent, isolating an intermediate [7,7']bis{[benzo[4,5]imidazo[2,1-a]isoindolyl]-11-one} compound, treating the intermediate purified [7,7']bis {[benzo[4,5]imidazo[2,1-a]isoindolyl]-11-one} compound with a second solvent, and isolating a purified [7,7']bis{[benzo[4,5]imidazo[2,1-a]isoindolyl]-11-one} compound. In an embodiment, the first solvent and the second solvent comprise at least one member selected from the group consisting of an aromatic hydrocarbon and a partially hydrogenated aromatic hydrocarbon. Therefore, in an embodiment, the purification step removes impurities, which are soluble in the first solvent and the second solvent. The presence of these impurities and the removal of these impurities can be conveniently followed by techniques such as HPLC. The impurities may comprise, among other chemical species, partly reacted intermediates formed during the course of the cyclization reaction to form the desired polycyclic heterocycle compound. These intermediates may not possess the right extent, or the right type of conjugation to exhibit the desired fluorescence emission in the green region of the visible spectrum, and the long Stokes shift of greater than or equal to 80 nanometers in one embodiment, greater than or equal to 100 nanometers in another embodiment, greater than or equal to 120 nanometers in still another embodiment. In an exemplary embodiment, the long Stokes shift is in a range from 80 nanometers to 180 nanometers. Further, the compounds thus purified have a low visible color, as represented by an absorption cut-off wavelength in the UV-visible spectrum of less than or equal to about 420 nanometers. Thus, purification helps in removal of such impurities and improves the performance of the isolated product as an authentication taggant in polymer compositions and articles made of such polymer compositions.

Dihydronaphthalene is a preferred first solvent. A preferred second solvent is one that is selected from the group consisting of toluene, xylenes, mesitylene, and mixtures thereof. In an embodiment, the purified [7,7']bis{[benzo[4,5]imidazo[2,1-a]isoindolyl]-11-one} compound prepared in accordance with this methodology has an absorption cut-off wavelength in the UV-visible spectrum of less than or equal to about 420 nanometers, a maximum fluorescence emission wavelength of greater than or equal to about 470 nanometers, and a Stokes shift of greater than or equal to about 80 nanometers.

Another aspect of the invention is a polymer composition comprising at least one [benzo[4,5]imidazo(heterocycle)] compound as a taggant, selected from the group consisting of structures I and II. The term "authenticatable polymer" means any polymer composition comprising a taggant composition, which is used to produce an authenticatable article. The polymer can comprise a thermoplastic polymer, a thermoset polymer, or mixtures thereof. The polymer can be a homopolymer, a copolymer, or mixtures thereof. Some possible examples of suitable polymers which can be utilized as the substrate polymer include, but are not limited to, amorphous, crystalline and semi-crystalline thermoplastic materials: polyvinyl chloride, polyolefins, chlorinated polyolefins, polyethylene terephthalate, polybutylene terephthalate, polycyclohexylmethylene terephthalate, polyamides, polysulfones, hydrogenated polysulfones, polyimides, polyetherimides, polyethersulfones, polyphenylene sulfides, polyether ketones, polyether ether ketones, ABS resins, polystyrenes, hydrogenated polystyrenes, poly(cyclohexylethylene), poly(styrene-co-acrylonitrile), poly(styrene-co-maleic anhydride)polybutadiene, poly(methylmethacrylate), poly(methylmethacrylate-co-imide)copolymers, polyacrylonitrile, polyacetals, polycarbonates, polyphenylene, polyarylene ethers, polyamideimide, poly(ethylene-co-vinyl acetate), polyvinyl acetate, liquid crystal polymers, ethylene-tetrafluoroethylene copolymers, polyarylates, polyvinyl fluoride, polyvinylidene fluoride, polyvinylidene chloride, polytetrafluoroethylenes, epoxy resins, phenolic resins, alkyds, polyurethane, mineral filled silicone resins, bismaleimide resins, cyanate ester resins, vinyl resins, and benzocyclobutene resins; and blends, mixtures and copolymers, reaction products, and composites comprising the foregoing polymers.

Suitable thermoplastic polymers are one or more members comprising engineering thermoplastic polymers. In an embodiment, the polymer is a thermoplastic polymer selected from the group consisting of polycarbonates, polyesters, polyamides, polyimides, polyamideimides, polysulfones, polyarylene ethers, polysiloxanes, and polyolefins; and blends and copolymers thereof.

Generally, the compounds of structures I and II may be present in the polymer in an amount from about 0.01 parts per million to about 20 weight percent of the [benzo[4,5]imidazo(heterocycle)] compound, relative to an overall weight of the polymer composition. The lower end of the range of the compounds in the polymer generally corresponds to the actual concentration of these compounds in the final polymer composition that has to be molded into articles. The higher end of the range generally corresponds to a masterbatch polymer composition, where a high amount, example up to 20 weight percent of the [benzo[4,5]imidazo(heterocycle)] compound can be present. The masterbatch approach for preparing molded articles is generally advantageous since it avoids difficulties, such as non-uniform distribution of the [benzo[4,5]imidazo(heterocycle)] additive in the matrix polymer, need to meter in accurately extremely small quantities of the additive into the matrix polymer stream, improve the consistency of the composition, and specifically limits the variation of taggant concentration in the final resin which ensure a more reliable authentication. Therefore, the masterbatch approach allows molders to more easily produce better quality molded products. The masterbatch may not only be used by molders to produce the final article containing the taggant, but also by resin manufacturers to produce the authenticatable resins.

The compounds of structures I and II also have relatively high decomposition temperatures, which for the purposes of this disclosure is defined as a temperature at which the material loses 10 percent of its weight when heated in air, relative to an initial weight, which is measured at an ambient temperature. In an embodiment, the [benzo[4,5]imidazo(heterocycle)] compounds have a decomposition temperature, as measured in air of greater than 350° C. in an embodiment, and about 280° C. to about 450° C. in another embodiment. Such high decomposition temperatures makes these compounds excellent candidates for application in polymer molding operations, especially for molding engineering thermoplastics, where molding temperatures in excess of 300° C. are frequently employed.

Authenticatable polymers and methods of authenticating provide valuable information. For example, the identification of a polymer as an authenticatable polymer or of an article as an authentictable article can provide one or more pieces of information such as the composition and source of the polymer, the source of an authenticatable article made from an authenticatable polymer, or of an article, whether a polymer or an article made therefrom is an unauthorized reproduction or duplication, the serial number (or lot number) of a polymer, the date of manufacture, and the like. In some instances, a failure to authenticate that a polymer or an article is an authenticatable polymer or authenticatable article will serve as proof of unauthorized duplication or copying.

Another embodiment of the invention is a method of authenticating that an article is an authenticatable article, where the authenticatable article comprise a taggant. The method comprises: irradiating a test portion of the article with a radiation at a wavelength below the cut-off wavelength (e.g., UV radiation) by using an optical tester comprising a radiation source and a photodetector (the optical tester being suitable for fluorescence measurement), measuring a test signal emitted by the article, and authenticating that the article is an authenticatable article if the test signal matches the standard signal; wherein the taggant comprises at least one [benzo[4,5]imidazo(heterocycle)] compound selected from the group consisting of structures I and II (disclosed earlier in this disclosure); and wherein the at least one [benzo[4,5]imidazo(heterocycle)] compound has an absorption cut-off wavelength in the UV-visible spectrum of less than or equal to about 420 nanometers, a maximum fluorescence emission wavelength of greater than or equal to about 470 nanometers, and a Stokes shift of greater than or equal to about 90 nanometers. The use of the authenticatable polymers disclosed herein in various polymer based articles allows for one or more parties at any point along the manufacturing chain, distribution chain, point of sale or point of use of the article to confirm or identify the presence or absence of the authenticatable polymer or article. In order to decrease the risks of identifying a counterfeit product as an authenticatable polymer or article, it may be desirable to perform the authentication using at least 2 sources: one with a peak wavelength below the cut-off wavelength, and another one with a peak wavelength in the visible/near UV range (i.e. a blue/violet emitting) source. For example, the source below the cut-off wavelength can be a 380 nm light emitting diode (LED) and the other source can be a blue/violet LED with a peak emission ranging between about 420 nm and about 470 nm. Such a combination would help distinguish between authenticatable polymers tagged with the long Stokes shift fluorophore against counterfeit that would use standard fluorophores with a shorter Stokes shift because very low fluorescence emission will be produced under the blue/violet source with the authenticatable polymer as compared to the counterfeit article. To authenticate an article or polymer, the optical tester equipped with the 2 sources will return 2 signals that can be compared against 2 reference signals for each source. The article is authenticated only if both signals can be validated. Authenticatable polymers may also comprise standard colorants to provide a custom visible color that might be desirable in certain applications or to distinguish certain customers over the others. In such cases, it is preferable if the optical tester also includes a white LED source as it is suitable to determine the visible color of an article. In one embodiment, the optical tester will comprise a UV LED and a white LED, and the photodetector will be an array of red, green, blue and clear filtered LEDs capable of measuring color. In a further embodiment, the optical tester will also include a blue LED. The optical tester can be incorporated in an optical drive, such as a CD or a DVD player and/or recorder, and allow or deny access to the data after authenticating the media.

Optical testers will comprise both an electromagnetic radiation source and a detector. Optical testers may be stationary units or hand held portable devices. In one embodiment, the optical tester is a data storage media player. Illustrative examples of data storage media include, but are not limited to, compact disks (CDs) and digital versatile disks (DVDs). In one embodiment, the optical tester can be a CD player. In another exemplary embodiment, the optical tester is a DVD player. In another embodiment, the optical tester can be a Blu ray disc player. Illustrative examples of suitable data storage media players are those data storage media players having a read laser with a wavelength in the range of from 330 nanometers (hereinafter abbreviated as "nm") to 450 nm in one embodiment, from 330 nm to 400 nm in another embodiment, and from 330 nm to 390 nm in yet another embodiment.

Illustrative examples of electromagnetic radiation sources include visible or invisible light sources with a broad spectral distribution, such as lamps and LED radiation; or a narrow spectral distribution (narrow band filtered light emitting diodes and lasers). The electromagnetic radiation source can be a laser or a LED radiation having a wavelength of about 330 nm to about 450 nm in one embodiment, from 330 nm to 400 nm in another embodiment, and from 330 nm to 390 nm in yet another embodiment. In an embodiment, at least one source used to perform the authentication must have a wavelength below or equal to about the cut-off wavelength in order to provide sufficient excitation to the taggant and produce a detectable emission.

Illustrative detectors that can be used include those that are capable of measuring, identifying and/or quantifying at least one of reflected electromagnetic radiation, transmitted electromagnetic radiation, emitted electromagnetic radiation, or combinations of such electromagnetic radiation as a detected signal. In one embodiment, the detector is capable of measuring, quantifying, and/or identifying at least one of intensity, spectral distribution, ratio of intensity, peak position, or the like, as well as combinations thereof. In some exemplary embodiments the detector is capable of measuring, identifying and/or quantifying optical interactions such as absorption, reflection, scattering, luminescence or the like as well as special properties of the detected signal such as polarization and the like. In one embodiment, the detector can be a photodetector.

Illustrative examples of the detector in one embodiment include electronic spectroscophotomers, such as UV-visible spectrophotomers; vibrational spectrophotometers, fluorescence spectrophotometers, luminescence spectrophotometers, and the like; and combinations thereof. Examples of vibrational spectrophotomers are Raman, infrared, Surface Enhanced Raman and Surface Enhanced Resonance Raman spectrophotomers. In one exemplary embodiment, the detector employed is a fluorescence spectrophotometer. In another exemplary embodiment, the detector can be a combination of fluorescence spectrophotometer and luminescence spectrophotometer.

The detection wavelength used in the disclosed method to authenticate an article is about 400 nm to about 550 nm. In an embodiment, the detection wavelength used to authenticate the article is in a range from about 450 nm to about 550 nm. If a single wavelength has to be selected based on the authentication method used, it is preferable to select the wavelength corresponding to the wavelength where the maximum fluorescence emission is expected.

The article to be authenticated can be in the shape of a formed article having thin edges and the detection of the changes in emission from exposure to a stimulus can be done at these thin edges of the article (edge emission) while the light source used for the excitation illuminates the article from the top, i.e., perpendicular to the surface of the article or at some angle to the normal to the surface (from 0 to about 80 degrees). In one exemplary embodiment, the formed article can be a data storage media device such as a CD or DVD. In another exemplary embodiment, the emission at the thin edges can be a fluorescence or luminescence emission.

Authenticatable articles or authenticatable polymers that can be authenticated or confirmed by the disclosed method comprise the [benzo[4,5]imidazo(heterocycle)] taggant, which absorbs radiation in the range between 330 nm and the UV cut-off wavelength (i.e., less than or equal to about 420 nm) to produce a test signal. The test signal comprises a pure fluorescence emission radiation in an embodiment, or a combination of fluorescence emission and some residual emission from the excitation source.

The signal detected by the detector is the test signal. The test signal is primarily a fluorescence emission signal, but depending on the authenticatable polymer composition, an absorption signal may also be used in addition to the fluorescence emission signal. In an exemplary embodiment, the test signal is a fluorescence emission. The [benzo[4,5]imidazo(heterocycle)] compounds produce a fluorescence emission test signal which in an embodiment is shifted by greater than about 100 nanometers towards a longer wavelength relative to the wavelength of the irradiating UV or laser radiation. This shift is often referred to as a long Stokes shift. In another embodiment, the long Stokes shift is greater than about 120 nanometers.

It will be appreciated that the individual dynamic natures of various ultraviolet radiation-sensitive [benzo[4,5]imidazo (heterocycle)] compounds may be used as a particularly unique authentication signature. The difficulty of predicting the particularly selected signature of a particular compound is advantageous in providing an authentication method that thwarts unauthorized duplication and copying activities.

An article may be authenticated as an authenticatable article if the UV radiation induced fluorescence emission test signal of the article is substantially the same as the UV radiation induced fluorescence emission standard signal of the authenticatable article. In one embodiment, the test signal and the standard signature can have a relative difference in value of less than or equal to about 5 percent. In other embodiments, variations between the test signal and the standard signal can be up to +/−20 percent, while in other embodiments, the variations can be about +/−10 percent. In some other embodiments, an excitation source having a peak wavelength that is just outside the traditional UV range, or that is below the absorption cut-off wavelength may be employed.

It is an aspect of the disclosed method that a test portion of the article to be authenticated be placed in interaction with the electromagnetic radiation source of the optical tester. The test portion of the article may be the entire article or may be only a portion of the article. In one exemplary embodiment, the test portion of the article to be authenticated will be a portion of the article containing a localized concentration of the radiation responsive compound. Thus, it is an advantage of the disclosed method that only a portion of the article to be authenticated needs to be irradiated by the radiation source. The size of the test portion can be as small as the spot created by a laser, i.e. about 1 micron, to about the size of an entire article. In one embodiment, the test portion will be about 0.1 centimeter to about 20 centimeters in diameter. In another embodiment, the test portion will be about 0.5 centimeter to about 15 centimeters in diameter.

The duration of the time to which a test portion is subjected to a radiation depends, inter alia, upon the wavelength of the irradiating radiation, the size of the test portion, the size and configuration of the article, the composition of any substrate polymers, the nature and concentration of the radiation sensitive compound (or taggant), and the like.

In one exemplary embodiment of the invention, the article to be authenticated may be a data storage media and the optical tester will be a data storage media player. In an embodiment, the spinning speed of the data storage media should be slow enough to give the UV or laser radiation sensitive compound enough time to produce the desirable level of fluorescence emission test signal. In one exemplary embodiment the data storage media can be spun during the method of authentication at a rate of between 1 rpm (revolutions per minute) and 40,000 rpm while in another embodiment, the data storage media can spin at a rate of between 100 rpm and 10,000 rpm. In a preferred embodiment, the optical media will spin at a rate ranging between 150 and 1000 rpm during authentication.

The method of authenticating disclosed herein may authenticate an article. In general, the goal of the method of authentication is to determine whether a test article is or is not an authenticatable article or whether a test article comprises an authenticatable polymer. In one exemplary embodiment, the article may be a polymer composition to be authenticated. The test article may comprise a polycarbonate, particularly a data storage media made using polycarbonate substrate polymer. In one exemplary embodiment, the article to be authenticated will be a DVD or a CD. In a further embodiment, the article will be a recordable disc (for instance, a recordable CD or DVD such as a CD-R, CD-RW, DVD-R, DVD+R, DVD-RW, and the like).

The disclosed method of authentication may be used more than once or only once. The concentration of the fluorophore compounds of structures I or II in an authenticatable polymer depends on the quantum efficiency of the radiation responsive compound, excitation and emission wavelengths, and employed detection techniques, and will generally be present in an amount of about 0.001 parts per million to about 1 percent by weight in an embodiment, about 0.5 parts per million to about 0.5 percent by weight in another embodiment, and about 1 part per million to about 1 percent by weight in yet another embodiment, relative to the overall weight of the authenticatable polymer or the authenticatable article.

In one embodiment, the fluorophore compound may be in at least a portion of the article to be authenticated. In another embodiment, the compound may be distributed throughout a portion of the article. In an exemplary embodiment, the fluorophore compound mahy be distributed homogeneously throughout a portion of the article. Similarly, the fluorophore compound may be on at least a portion of a surface of the article to be authenticated or may be applied to an entire surface. In another embodiment, the UV or laser radiation responsive compound may be distributed evenly on a surface of the article, while in another embodiment, the UV or laser radiation responsive compound may be contained in a localized area on the surface of at least a portion of the article.

In one exemplary embodiment, at least one portion or component of the article to be authenticated or the authenticatable article will comprise an authenticatable polymer comprising a substrate polymer and a UV or laser radiation responsive [benzo[4,5]imidazo(heterocycle)] compound, as described above.

In an exemplary embodiment, the substrate polymer is a polycarbonate polymer. Polycarbonates having a wide variety of molecular structure, molecular weight, and physical properties can be produced by one of skill in the art using art-recognized techniques. Polycarbonate homopolymers, copolymers, and blends thereof, based on bisphenol A as a monomer or a comonomer are preferred substrates since they are easily prepared and are readily available commercially. Polycarbonate compositions suitable for use as the substrate polymer may also include various additives ordinarily incorporated in resin compositions of this type. Such additives are, for example, fillers or reinforcing agents; heat stabilizers; antioxidants; light stabilizers; plasticizers; antistatic agents; flame retardants; mold releasing agents; additional resins; blowing agents; and the like, as well as combinations comprising the foregoing additives. Combinations of any of the foregoing additives may be used. Such additives may be mixed at a suitable time during the mixing of the components for forming the composition.

Examples of fillers or reinforcing agents include glass fibers, asbestos, carbon fibers, silica, talc and calcium carbonate. Examples of heat stabilizers include triphenyl phosphite, tris-(2,6-dimethylphenyl)phosphite, tris-(mixed mono- and di-nonylphenyl)phosphite, dimethylbenene phosphonate and trimethyl phosphate.

Examples of antioxidants include octadecyl-3-(3,5-di-tert-butyl-4-hydroxyphenyl)propionate, and pentaerythrityl-tetrakis[3-(3,5-di-tert-butyl-4-hydroxyphenyl)propionate]. Other possible antioxidants include, for example, organo-phosphites, e.g., tris(nonyl-phenyl)phosphite, tris(2,4-di-t-butylphenyl)phosphite, bis(2,4-di-t-butylphenyl)pentaerythritol diphosphite, distearyl pentaerythritol diphosphite and the like; alkylated monophenols, polyphenols and alkylated reaction products of polyphenols with dienes, such as, for example, tetrakis[methylene(3,5-di-tert-butyl-4-hydroxyhydrocinnamate)]methane, 3,5-di-tert-butyl-4-hydroxyhydrocinnamate octadecyl, 2,4-di-tert-butylphenyl phosphite, and the like; butylated reaction products of para-cresol and dicyclopentadiene; alkylated hydroquinones; hydroxylated thiodiphenyl ethers; alkylidene-bisphenols; benzyl compounds; esters of beta-(3,5-di-tert-butyl-4-hydroxyphenyl)-propionic acid with monohydric or polyhydric alcohols; esters of beta-(5-tert-butyl-4-hydroxy-3-methylphenyl)-propionic acid with monohydric or polyhydric alcohols; esters of thioalkyl or thioaryl compounds, such as, for example, distearylthiopropionate, dilaurylthiopropionate, ditridecylthiodipropionate, and the like; amides of beta-(3,5-di-tert-butyl-4-hydroxyphenyl)-propionic acid; and the like, as well as combinations of the foregoing.

Examples of light stabilizers include 2-(2-hydroxy-5-methylphenyl)benzotriazole, 2-(2-hydroxy-5-tert-octylphenyl)-benzotriazole and 2-hydroxy-4-n-octoxy benzophenone. Examples of plasticizers include dioctyl-4,5-epoxyhexahydrophthalate, tris-(octoxycarbonylethyl) isocyanurate, tristearin and epoxidized soybean oil. Examples of antistatic agents include glycerol monostearate, sodium stearyl sulfonate, and sodium dodecylbenzenesulfonate. Examples of mold releasing agents include stearyl stearate, beeswax, montan wax and paraffin wax. Examples of other resins include but are not limited to polypropylene, polystyrene, polymethyl methacrylate, and polyphenylene oxide.

Other additives ordinarily incorporated in resin compositions of this type may also be used. Such additives may include antioxidants, heat stabilizers, anti-static agents (tetra alkylammonium benzene sulfonate salts, tetra alkylphosphonium benzene sulfonate salts, and the like), mold releasing agents (pentaerythritol tetrastearate; glycerol monstearate, and the like), and the like, and combinations comprising any of the foregoing. Other potential additives which may be employed comprise: stabilizers such as light and thermal stabilizers (e.g., acidic phosphorous-based compounds); hindered phenols; zinc oxide, zinc sulfide particles, or combination thereof; lubricants (mineral oil, and the like), plasticizers, dyes used as a coloring material (anthraquinones, anthrapyridones, methane dyes, quinophthalones, azo dyes, perinones, and the like); among others, as well as combinations of the foregoing additives.

For example, in one exemplary embodiment the authenticatable polymer composition can comprise heat stabilizer from about 0.01 weight percent to about 0.1 weight percent; an antistatic agent from about 0.01 weight percent to about 1 weight percent; and a mold releasing agent from about 0.1 weight percent to about 1 weight percent of a mold releasing agent; based upon the weight of the authenticatable polymer.

In order to aid in the processing of the authenticatable polymer, particularly when the substrate polymer is polycarbonate, catalyst(s) may also be employed, namely in the extruder or other mixing device. The catalyst typically assists in controlling the viscosity of the resulting material. Possible catalysts include hydroxides, such as tetraalkylammonium hydroxide, tetraalkylphosphonium hydroxide, and the like, with diethyldimethylammonium hydroxide and tetrabutylphosphonium hydroxide preferred. The catalyst(s) can be employed alone or in combination with quenchers such as acids, such as phosphoric acid, and the like. Additionally, water may be injected into the polymer melt during compounding and removed as water vapor through a vent to remove residual volatile compounds.

The authenticatable polymers disclosed herein are produced by using a reaction vessel capable of adequately mixing various precursors, such as a single or twin screw extruder, kneader, blender, or the like.

Methods for incorporating the [benzo[4,5]imidazo(heterocycle)] compounds into the substrate polymer include, for example, solution casting, admixing, blending, or copolymerization. In one embodiment, the [benzo[4,5]imidazo (heterocycle)] compounds may be incorporated into the polymer in the polymer manufacturing stage, during the polymer compounding step, during polymer processing into articles, or combinations thereof. The [benzo[4,5]imidazo (heterocycle)] compounds may be introduced using a concentrate that is, masterbatch, as described earlier, or during the polymer compounding stage, or during the article forming process.

For example, the polymer precursors for the substrate polymer can be premixed with the [benzo[4,5]imidazo(heterocycle)] compounds (e.g., in a pellet, powder, and/or liquid form) and simultaneously fed using a gravimetric or volumetric feeder into the extruder, or the [benzo[4,5] imidazo(heterocycle)] compounds may be optionally added in the feed throat or through an alternate injection port of the injection molding machine or other molding apparatus. Optionally, in one embodiment, a substrate polymer can be produced and the [benzo[4,5]imidazo(heterocycle)] compounds can be dispersed on a portion of a substrate polymer by coating, molding, or welding on a portion of an authenticatable polymer.

In another approach, the [benzo[4,5]imidazo(heterocycle)] compounds may be incorporated into the substrate polymer by adding the compounds in the melt during compounding. In one exemplary embodiment, the [benzo[4, 5]imidazo(heterocycle)] compounds may be incorporated by compounding using a twin-screw extruder, by adding the [benzo[4,5]imidazo(heterocycle)] compounds to the melt via a side feeder. In another exemplary embodiment, the [benzo[4,5]imidazo(heterocycle)] compounds may be added downstream of the extruder via a side feeder. In another particular embodiment, a single screw extruder may be used, especially if the melting point of the fluorophore is low compared to the extrusion temperature.

When the substrate polymer precursors are employed, the extruder should be maintained at a sufficiently high temperature to melt the polymer precursors without causing decomposition thereof. For polycarbonate, for example, temperatures of about 220° C. to about 360° C. can be used in one embodiment. In another embodiment, temperatures of about 260° C. to about 320° C. are utilized. Similarly, the residence time in the extruder should be controlled to minimize decomposition. Residence times of up to about 10 minutes can be employed, with up to about 5 minutes used in one embodiment, up to about 2 minutes used in another embodiment, and up to about 1 minute used in yet another embodiment. Prior to extrusion into the desired form (typically pellets, sheet, web, or the like), the resulting mixture can optionally be filtered, such as by melt filtering and/or the use of a screen pack, or the like, to remove undesirable contaminants or decomposition products.

In some embodiments, under the conditions used to prepare polymer pellets having the compounds of structures I or II, especially those having hydroxy groups, or carboxylic acid groups, a chemical reaction between the carboxylic acid groups and appropriate functional groups (such as example, amino, amido, hydroxy, etc.) that may be present in the polymer chains of the polymer substrate may occur. This may result in formation of a chemically bonded derivative of the fluorescent compounds I or II such that the fluorescence property is essentially retained in the resulting polymer composition. Fluorophore compounds having a hydroxy group can react with diaryl carbonates having activating groups (usually electron withdrawing groups), such as bis(methylsalicyl)carbonate (or BMSC), which are used for preparing polycarbonate homopolymers and copolymers. In such a situation, the fluorophore compound may become chemically attached to the polycarbonate resin matrix.

The compounds of structures I and II are valuable for producing a variety of articles. Articles that can be beneficially produced include molded articles, extruded articles, and coated articles. Polymer compositions comprising the [benzo[4,5]imidazo(heterocycle)] compounds can be injection molded or extruded using any standard equipment, design, or configuration available commercially or known to one of skill in the art. Coating compositions comprising the [benzo[4,5]imidazo(heterocycle)] compounds can be either solvent based or powder-based. The choice of solvent, equipment, and application conditions needed to produce a desired coating can be ascertained by one skilled in the art. The molded articles produced in this manner are, in an embodiment, authenticatable articles which can be authenticated as being original. The authenticatable article comprises from 0.001 parts per million to about 1 weight percent in an embodiment, from 0.5 parts per million to about 0.5 weight percent in another embodiment, and from 1 part per million to about 1 weight percent in still another embodiment, of the [benzo[4,5]imidazo(heterocycle)] compound, relative to an overall weight of the authenticatable article.

The authenticatable polymers may be used for any application in which the physical and chemical properties of the material are desired. In one embodiment, the authenticatable polymers may be used to make articles to be authenticated. In one embodiment, the article comprising the authenticatable polymers can be data storage media. Other articles comprising the authenticatable polymers include packaging material (and especially drug packaging), automotive parts like lenses, telecom accessories (like cell phone covers), computers and consumer electronics, construction materials, medical devices, eyeware products, optical disks, security documents, security inks, currency bills, automotive parts, telecom and consumer electronic products, packaging materials for liquor, cosmetics, pharmaceuticals and medical devices; films and sheets (including those used in display applications) and the like.

Data storage media, which can be authenticated using the disclosed authentication method, can be formed using various molding techniques, processing techniques, or combinations thereof. Suitable molding techniques include injection molding, film casting, extrusion, press molding, blow molding, stamping, and the like. One possible process comprises an injection molding-compression technique where a mold is filled with a molten polymer that in one embodiment may be the authenticatable polymer. The mold may contain a preform, inserts, fillers, etc. The polymer is cooled and, while still in an at least partially molten state, compressed to imprint the desired surface features (e.g., pits, grooves, edge features, smoothness, and the like), arranged in spiral concentric or other orientation, onto the desired portion(s) of the formed part, i.e. one or both sides in the desired areas. The formed part is then cooled to room temperature. Once the formed part has been produced, additional processing, such as electroplating, coating techniques (spin coating, spray coating, vapor deposition, screen printing, painting, dipping, and the like), lamination, sputtering, and combinations comprising the foregoing processing techniques, among others known in the art, may be employed to dispose desired layers on the substrate.

An example of a data storage media comprises an injection molded substrate that may optionally comprise a hollow (bubbles, cavity, and the like) or filled (metal, plastics, glass, ceramic, and the like, in various forms such as fibers, spheres, particles, and the like) core. In one embodiment, the molded substrate may comprise polycarbonate.

In one embodiment when a formed authenticatable article or test article is a data storage media, the authenticatable polymer will preferably be used to form the substrate(s) that will be read through by a laser in a data storage media player device as it is significantly more difficult to fake the response of an authenticatable polymer and to ensure that the employed technology does not impact playability of the media. In a data storage media having two substrates, such as a DVD, one or both substrates can be formed using the authenticatable polymers. In one exemplary embodiment, the substrate of a DVD formed of the authenticatable polymer will be the substrate read through by a laser in a DVD player device.

Disposed on a substrate of the data storage media are various layers including a read through substrate layer, bonding layer, data layer, dielectric layer(s), a semi reflective layer, a bonding layer, a reflective layer(s), and/or a protective layer, as well as combinations comprising the foregoing layers. The substrate layer itself may comprise one or more additional layers. These additional layers comprise various materials, and are disposed in accordance with the type of media produced. For example, the layers may constitute a surface media, the surface media comprising a protective layer, dielectric layer, data storage layer, dielectric layer, and then a reflective layer disposed in contact with the substrate, with an optional decorative layer disposed on the opposite side of the substrate. Meanwhile, for one type of optical media, the layers may be optional decorative layer, protective layer, reflective layer, dielectric layer, and data storage layer, with a subsequent dielectric layer in contact with the substrate. Optical media may include, but are not limited to, any conventional pre-recorded, re-writable, or recordable formats such as: CD, CD-ROM, CD-R, CD-RW, DVD, DVD-R, DVD-RW, DVD-RAM, DVD-ROM, high-density DVD, enhanced video disk (EVD), super audio CD (SACD), magneto-optical, Blu Ray, and others. It is understood that the form of the media is not limited to disk-shape, but may be any shape which can be accommodated in a readout device.

The data storage layer(s) may comprise any material capable of storing retrievable data, such as an optical layer, magnetic layer, or a magneto-optic layer. Possible data storage layers include, but are not limited to, oxides (such as silicone oxide), rare earth elements—transition metal alloys, nickel, cobalt, chromium, tantalum, platinum, terbium, gadolinium, iron, boron, others, alloys, organic dyes (e.g., cyanine or phthalocyanine type dyes), inorganic phase change compounds (e.g., TeSeSn, InAgSb, and the like) and combinations comprising the foregoing.

The protective layer(s) protect against dust, oils, and other contaminants. The thickness of the protective layer(s) is usually determined, at least in part, by the type of read/write mechanism employed, e.g., magnetic, optic, or magneto-optic. Possible protective layers include anti-corrosive materials such as gold, silver, nitrides (e.g., silicon nitrides and aluminum nitrides, among others), carbides (e.g., silicon carbide and others), oxides (e.g., silicon dioxide and others), polymeric materials (e.g., polyacrylates or polycarbonates), carbon film (diamond, diamond-like carbon, and the like), among others, and combinations comprising the foregoing.

The dielectric layer(s) may be disposed on one or both sides of the data storage layer and are often employed as heat controllers. Possible dielectric layers include nitrides (e.g., silicon nitride, aluminum nitride, and others); oxides (e.g., aluminum oxide); carbides (e.g., silicon carbide); and combinations comprising of the foregoing materials, among other materials compatible within the environment and preferably not reactive with the surrounding layers.

The reflective layer(s) should have a sufficient thickness to reflect a sufficient amount of energy (e.g., light) to enable data retrieval. Possible reflective layers include any material capable of reflecting the particular energy field, including metals (e.g., aluminum, silver, gold, titanium, silicon, and alloys and mixtures comprising the foregoing metals, and others).

In addition to the data storage layer(s), dielectric layer(s), protective layer(s) and reflective layer(s), other layers can be employed such as lubrication layer and others. Useful lubricants include fluoro compounds, especially fluoro oils and greases, and the like.

In one embodiment, the authenticatable polymers will be formed into the substrate of a data storage media. In one exemplary embodiment, the authenticatable polymer will comprise the substrate of an optical storage media.

In one particularly exemplary embodiment, the authenticatable polymer will comprise at least one substrate of a digital versatile disk (DVD). Illustrative DVDs comprising the authenticatable polymers disclosed herein comprise two bonded plastic substrates (or resin layers), each typically having a thickness less than or equal to about 0.8 millimeter (mm), with a thickness of less than or equal to about 0.7 mm preferred. A thickness of greater than or equal to about 0.5 mm is also preferred. At least one of the two bonded plastic substrates comprises one or more layers of data. The first layer, generally called layer zero (or L0), is closest to the side of the disk from which the data is read (readout surface). The second layer, generally called layer 1 (L1), is further from the readout surface. Disposed between L0 (3) and L1 (5) are typically an adhesive and optionally a protective coating or separating layer. Single sided DVD's (i.e., those that will be read from a single readout surface disposed on one side of the DVD), can additionally comprise a label disposed on the side of the DVD opposite the readout surface. In one embodiment, one or both of the first layer and the second layer will be comprised of the authenticatable polymers. In one exemplary embodiment, the first layer will be comprised of the authenticatable polymer.

In the case of a single layer read from a readout surface (e.g. DVD 5, DVD 10), a stamped surface is covered with a thin reflective data layer by a sputtering or other deposition process. This creates a metallic coating typically about 60 to about 100 angstroms (Å) thick. For two data layer DVDs that are read from the same readout surface (e.g. DVD 9, DVD 14, DVD 18), the laser must be able to reflect from the first layer when reading it, but also focus (or transmit) through the first layer when reading the second layer. Therefore, the first layer is "semi-transparent" (i.e., semi-reflective), while the second layer is "fully-reflective". Under current standards set by the Consortium for Optical Media, metallization combination for the fully-reflective and semi-reflective data layers, as measured per the electrical parameter R14H (as described in ECMA specifications #267), should be about 18 percent (%) to about 30% at the wavelength of the laser. In the present DVD's, the laser wavelength generally employed is less than or equal to about 700 nm, with about 370 nm to about 680 nm preferred, and about 600 nm to about 680 nm more preferred. Although these metallization standards were set for DVD data layers employed with colorless, optical quality resin, they are equally applied to DVD systems with colored resin.

When color is added to the resin, light transmission through and reflected from the substrate is effected. The metallization nature and thickness on the semi-reflective and fully reflective (L0 and L1) layers is adapted for the light transmission of the substrate. Desired reflectivity can be obtained by balancing the metallization thickness with the reflectivity of the semi-reflective data layer, and by adjusting the thickness of the fully reflective data layer to ensure its reflectivity is within the desired specification.

Metallization for the individual data layer(s) can be obtained using various reflective materials. Materials, e.g., metals, alloys, and the like, having sufficient reflectivity to be employed as the semi-reflective and/or fully reflective data layers, and which can preferably be sputtered onto the substrate, can be employed. Some possible reflective materials comprise gold, silver, platinum, silicon, aluminum, and the like, as well as alloys and combinations comprising at least one of the foregoing materials. For example, the first/second reflective data layer metallization can be gold/aluminum, silver alloy/aluminum, silver alloy/silver alloy, or the like.

In addition to the overall reflectivity of each layer, the difference in reflectivity between subsequent reflective data layers should be controlled, in order to ensure sufficient reflectivity of the subsequent layer. Preferably, the difference in reflectivity between subsequent layers (e.g., the first and second layers) is less than or equal to about 5%, with less than or equal to about 4% preferred, and less than or equal to about 3.0% more preferred. It is further preferred to have a reflectivity difference between the adjacent reflective data layers of greater than or equal to about 0.5%, with greater than or equal to about 1% more preferred. It should be noted that although described in relation to two layers, it is understood that more than two layers could be employed, and that the difference in reflectivity between subsequent layers should be as set forth above.

The reflective data layers are typically sputtered or otherwise disposed on a pattern (e.g., surface features such as pits, grooves, asperities, start/stop orientator, and/or the like) formed into a surface of the substrate via molding, embossing, or the like. Depositions, for example, can comprise sputtering a semi-reflective data layer over a first patterned surface. A separator layer or protective coating can then be disposed over the semi-reflective data layer. If a multiple data layer DVD (e.g., DVD 14, DVD 18, or the like) is to be formed, a 2nd patterned surface can be formed (e.g., stamped or the like) in the side of the separator layer opposite the semi-reflective data layer. A fully reflective data layer can then be sputtered or otherwise deposited on the separator layer. Alternatively, for DVD 14 construction, the fully reflective data layer can be deposited on a patterned surface of a 2nd substrate (or resin layer). A separate layer or protective coating is then disposed on one or both of the semi-reflective data layer and the fully reflective data layer. A bonding agent or adhesive can then be disposed between the two substrates and they can be bonded together to form a disk. Optionally, several semi-reflective data layers can be deposited with a separator layer between each subsequent layer.

The reflectivity of the reflective data layer(s) can be about 5% to about 100%, depending upon the number of reflective layers. If a single reflective data layer is employed, the reflectivity is preferably about 30% to about 100%, with about 35% to about 90% more preferred, and about 45% to about 85% even more preferred. If a dual reflective data layer is employed, the reflectivity of the data layers is preferably about 5% to about 45%, with about 10% to about 40% more preferred, about 15% to about 35% even more preferred, and about 18% to about 30% especially preferred. Finally, if multiple reflective data layers (e.g., greater than 2 reflective data layers readable from a single reading surface) are employed, the reflectivity is preferably about 5% to about 30%, with about 5% to about 25% more preferred. The especially preferred ranges are currently based upon the ECMA specification #267, wherein the reflectivity is either about 18% to about 30% reflectivity for a dual layered DVD (e.g., at least one fully reflective layer and at least one semi-reflective layer) or about 45% to about 85% reflectivity for a single layer DVD (e.g., one fully reflective layer).

In one embodiment, the polymers used to make these DVD substrates will enable the transmission of about 60% to less than 94% of light therethrough, in the wavelength region of the laser. Within that transmission range, preferably, the transmissivity is greater than or equal to about 70%, with greater than or equal to about 74% more preferred, and greater than or equal to about 78% especially preferred. Depending upon the type and amount of colorant employed, the transmissivity can be less than or equal to about 92%, with less than or equal to about 88% and even less than or equal to about 85% possible, depending upon the type of colorant. It should be noted that as the transmissivity of the substrate decreases, the ability to attain the desired adhesion of the substrates becomes more difficult. Preferably, the substrate comprises polycarbonate, with a primarily polycarbonate (e.g., greater than or equal to about 80% polycarbonate) substrate especially preferred.

As previously discussed, the fluorophore compounds may be in or on the article to be authenticated or the authenticatable article. Such an article or authenticatable article may be a data storage media disk, where the data storage media comprises a read through substrate layer and a reflective layer. The data storage media may further comprise one or more additional substrate layers, a bonding layer, or a semi-reflective layer. The UV or laser radiation responsive compound may be located on a surface of the read through substrate layer of the data storage media, or in the read through substrate layer of the data storage media. In one embodiment, the read through substrate layer is comprised of polycarbonate.

The compositions, methods and articles disclosed herein provide for authentication techniques useful in the authentication and confirmation of the source, and identify polymer-based substrates and articles, especially polycarbonate based substrates and articles made from such substrates.

The presence of fluorophore compounds in a particular substrate or data storage media provides for a variety of options with respect to a particularly selected authentication signal (in terms of a pre-defined long Stokes shift) for an authenticatable polymer. As a result, counterfeiters and illegitimate producers and sellers will find it more difficult to 'mimic' the authentication signal for an authenticatable polymer and articles legitimately made therefrom. The difficulty of predicting the particularly selected test signal indicative of a particular fluorophore compound is advantageous in providing an authentication method that thwarts unauthorized duplication and copying activities.

The following Examples are provided to further illustrate the invention.

EXAMPLES

All necessary raw materials and reagents used were of laboratory grade purity, and were obtained from Aldrich—Sigma Company, USA; and Lancaster Chemical Company, UK. Proton NMR spectra for all the starting materials and products described herein were measured using a 300 megahertz Bruker NMR spectrometer and $d_6$-dimethylsulfoxide as solvent. Compounds were further characterized by a liquid chromatograph-mass spectrometer (LC-MS) system, comprising a liquid chromatograph and a Quattro Ultima Pt mass spectrometer. An Xterra C18 (50 mm×4.6 mm; 5 microns) column was used for the separating the components by liquid chromatography. The separated components were then analyzed by mass spectrometry. Ultraviolet-visible (UV-VIS) spectra were recorded using a double beam Perkin-Elmer Lambda 900 UV-VIS-NIR spectrophotometer.

Infrared (IR) spectra were obtained using a Perkin Elmer Spectrum GX series instrument by employing the attenuated total reflectance mode.

Fluorescence spectra were recorded using a Hitachi F-4500 spectrophotometer and an excitation radiation having a wavelength of 365 nm. Measurements were made on 1 millimeter thick molded chips having the fluorescing compound. A reflective background was used to measure the fluorescence response.

Thermogravimetric analysis (TGA) on the [benzo[4,5] imidazo(heterocycle)] compounds were carried out to determine their thermal stability. As disclosed herein, thermal stability is given by the temperature at which the sample lost 10 percent of its initial weight. The analyses were carried out using a TGA 2950 instrument equipped with an auto sampler, and available from TA Instruments. The technique was used to measure the amount of weight change in a material as a function of temperature in air. The sample was equilibrated to an initial temperature of 40° C., then heated at the rate of 10° C. per minute upto a maximum temperature of 500° C., and thereafter equilibrated at 500° C. The weight of the sample was monitored continuously throughout this process. The technique measures any weight change that can occur during the heating process.

Example 1

This Example Describes the Preparation of [7,7']Bi [benzo[4,5]imidazo[2,1-a]isoindolyl]11,11'-dione.

A mixture of 3,3'4,4'-tetraaminobiphenyl (1 gram), phthalic anhydride (1.48 gm) and acetic acid (25 milliliters) was heated under reflux with stirring for 10 hours. After being cooled to room temperature, the reaction mixture was filtered, and the solid product was recovered, washed with acetic acid, then water, and dried at 120° C. for 8 hours to furnish the product (1.8 grams).

This crude product was stirred in tetrahydronaphthalene (10 milliliters) maintained at 160° C. After being stirred for 4 hours, the temperature of the mixture was brought to 100° C., filtered, and the solid filter cake was washed with tetrahydronaphthalene (5 milliliters). The solid product was heated in refluxing toluene (10 milliliters) for 1 hour, then cooled to ambient temperature, filtered, and finally dried at 120° C. for 8 hours to yield purified product in a yield of 1.5 grams.

Example 2

This Example Describes the Preparation of 7,7'-Dibenzoyl-[2,2']bi[benzo[4,5]imidazo[2,1-a]isoindolyl]-11,11'-dione.

A mixture of 3,3',4,4'-biphenyltetracarboxylicdianhydride (3 grams), acetic acid (50 milliliter) and 3,4-diaminobenzophenone (5.19 gram) was heated under reflux with stirring for 10 hours. After being cooled to ambient temperature, the solid product that precipitated out was filtered, washed with acetic acid, then water, and dried at 120° C. for 8 hours. The yield of the crude product was 6.5 grams.

The crude product was stirred in tetrahydronaphthalene (20 milliliter) maintained at 160° C. for 4 hours. The temperature of the mixture was brought to 100° C., filtered, and washed with 5 milliliters of tetrahydronaphthalene. The filter cake was stirred in refluxing toluene (25 milliliters), and the insoluble solid product was filtered and dried at 120° C. for 8 hours to yield 5 grams of the purified product.

Example 3

This Example describes the procedure used for preparing the extruded polymer samples incorporating the [benzo[4,5]imidazo(heterocycle)] compounds prepared as described above. The method is exemplified with [7,7']-Bi [benzo [4,5] imidazo [2,1-a]isoindolyl]11,11'-dione A mixture of 1 kilogram of bisphenol A homopolycarbonate (HF1110R, commercially available from GE Plastics) and [7,7']Bi [benzo [4,5] imidazo [2,1-a]isoindolyl]11, 11'-dione additive (prepared as described in Example 1), such that the additive comprised about 0.005 weight percent of the overall sample was taken in a polyethylene bag and shaken vigorously for about 3–4 minutes. The resulting material was then compounded by using a W & P ZSK-25 Mega Compounder under vacuum under the conditions specified in Table 1 to produce polymer pellets.

TABLE 1

| | |
|---|---|
| Feed zone temperature (° C.) | 128 |
| Zone 1 temperature (° C.) | 280 |
| Zone 2 temperature (° C.) | 285 |
| Zone 3 temperature (° C.) | 285 |
| Zone 4 temperature (° C.) | 290 |
| Throat/Die temperature (° C.) | 290 |
| Screw speed (Revolutions per minute) | 300 |
| Temperature of Melt (° C.) | 300 |
| Torque (Nm) | 58–62 |

Example 4

This Example describes the general procedure used for producing molded chips from the extruded pellets prepared as described in Example 3.

The extruded pellets were dried in an oven maintained at 120° C. for about 4 hours. Then the dried pellets were subjected to molding using a LTM-Demag molding machine under the conditions shown in Table 2.

Examples 5 and 6 correspond to molded plaques having the [benzo[4,5]imidazo(heterocycle)] compounds of Examples 1 and 2, respectively. The molded plaques, prepared as described in Example 4 were used to measure the fluorescence emission spectrum displayed by the [benzo[4,5]imidazo(heterocycle)] compound present in the plaque. The UV-visible absorption maximum represents the highest intensity absorption exhibited by the [benzo[4,5]imidazo (heterocycle)] compound as measured using N,N-dimethylformamide as solvent. The absorption cut-off wavelength ($\lambda_a$) represents the wavelength corresponding to 5 percent of the intensity of the maximum UV-visible absorption signal. The difference between the wavelength at which a particular [benzo[4,5]imidazo(heterocycle)] compound shows the highest intensity UV-visible absorption maximum ($\lambda_{max}$) and a fluorescence emission ($\lambda_e$) peak gives the Stokes shift (in nanometers). The results are summarized in Table 4, where "$T_d$" represents the temperature at which the [benzo [4,5]imidazo(heterocycle)] compound lost 10 percent of its weight, relative to an initial weight of the compound at ambient temperature; and "($\lambda_v$)" represents the visible cut-off color of the compound. These results are shown in Table 3.

TABLE 2

| | |
|---|---|
| Feed zone temperature (° C.) | 110 |
| Zone 1 temperature (° C.) | 300 |

TABLE 2-continued

| | |
|---|---|
| Zone 2 temperature (° C.) | 290 |
| Zone 3 temperature (° C.) | 275 |
| Nozzle Temperature (° C.) | 295 |
| Temperature of Melt (° C.) | 300 |
| Mold temperature (° C.) | 85 |
| Sample drying time (hours) | 4 |
| Sample drying temperature (° C.) | 120 |
| Cycle time (seconds) | 125 |
| Injection time (seconds) | 1.2 |
| Injection speed (revolutions per minute) | 25 |
| Injection pressure (bar) | 50 |
| Screw speed (Revolutions per minute) | 300 |
| Holding pressure (bar) | 40 |
| Holding time (seconds) | 10 |
| Cooling time (seconds) | 15 |
| Thickness of step chip inserts (millimeters) | 1, 2, and 3 |
| Thickness of single insert (millimeters) | 2.54 |

TABLE 3

| Example Number | Example Number of Compound used | $\lambda_{max}$ (nm) | $\lambda_v$ (nm) | $\lambda_a$ (nm) | Stokes shift (nm) | $T_d$ (° C.) |
|---|---|---|---|---|---|---|
| 5 | 1 | 328 | 387 | 468, 492 | 140, 164 | 310 |
| 6 | 2 | 341 | 415 | 467, 484 | 126, 143 | 420 |

The results shown in Table 3 clearly illustrate that the [benzo[4,5]imidazo(heterocycle)] compounds of Examples 1 and 2 exhibit the desirable combination of low absorption cut-off wavelength of less than 420 nanometers, i.e., the molded chips having the taggant compound show none or very little color; a fluorescence emission in the green region of the visible spectrum, and a long Stokes shift of greater than 80 nanometers.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A composition comprising at least one [benzo[4,5]imidazo(heterocycle)] compound, said at least one [benzo[4,5]imidazo(heterocycle)] compound being selected from the group consisting of structures I and II:

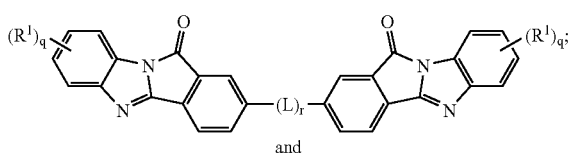

and

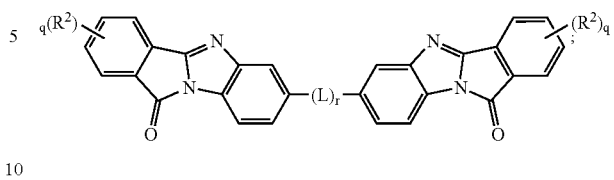

wherein each $R^1$ is independently selected from the group consisting of a hydrogen atom, electron withdrawing group, aliphatic group, cycloaliphatic group, aromatic group, divalent 1,2-cycloalkylidene group, or combinations thereof;

wherein each $R^2$ is independently selected from the group consisting of trifluoromethyl, acetyl, benzoyl, propanoyl, butanoyl, pentanoyl, methoxycarbonyl, ethoxycarbonyl, acetoacetyl, nitro, chloro, bromo, iodo, fluoro, alkylsulfonyl, arylsulfonyl, aliphatic group, cycloaliphatic group, aromatic group, divalent 1,2-cycloalkylidene group, or combinations thereof;

"q" is independently an integer from 1–4, L is a linking group, and "r" is independently 0 or 1; and wherein said at least one [benzo[4,5]imidazo(heterocycle)] compound is present in said composition at a concentration sufficient to cause said composition to exhibit upon exposure to an excitation radiation having a wavelength of from about 330 nanometers to about 390 nanometers, a a maximum fluorescence emission wavelength of greater than or equal to about 470 nanometers; and a Stokes shift of greater than or equal to about 80 nanometers; wherein the wavelengths are measured in bisphenol A polycarbonate matrix.

2. The composition of claim 1, wherein said [benzo[4,5]imidazo(heterocycle)] compound has a 10 percent weight loss decomposition temperature, as measured in air of about 280° C. to about 450° C.

3. The composition of claim 1, wherein "q"=1.

4. The composition of claim 3, wherein "L" is independently selected from the group consisting of C=O, S, O, $SO_2$, $CR^3R^4$, wherein $R^3$ and $R^4$ are independently selected from the group consisting of a hydrogen atom, an aliphatic group, an aromatic group, a cycloaliphatic group, and combinations thereof; and "r" is 1.

5. The composition of claim 3, wherein "L" is independently selected from the group consisting of C=O, O, $SO_2$, $CR^3R^4$, wherein $R^3$ and $R^4$ are independently selected from the group consisting of a hydrogen atom, an aliphatic group, an aromatic group, a cycloaliphatic group, and combinations thereof: and "r" is 0.

6. The composition of claim 5, wherein $R^1$ is selected from the group consisting of an ester group, a carboxylic acid group, a ketone group, a halogen group, a nitro group, a cyano group, a trifluoromethyl group, a sulfone group, and combinations thereof.

7. The composition of claim 6, wherein said ketone group has a formula $COR^7$, wherein $R^7$ is selected from the group consisting of a $C_1$–$C_{12}$ aliphatic, cycloaliphatic, or aromatic group.

8. The composition of claim 6, wherein said ester group has a formula $COOR^8$, wherein $R^8$ is selected from the group consisting of a $C_1$–$C_{12}$ aliphatic, cycloaliphatic, or aromatic group.

9. The composition of claim 1, wherein said at said at least one [benzo[4,5]imidazo(heterocycle)] compound is structures XII:

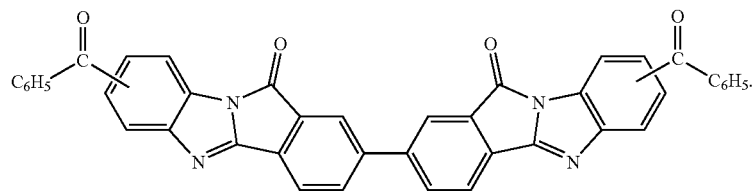

XIII

10. The composition of claim 1, wherein said at least one [benzo[4,5]imidazo(heterocycle)] compound has an absorption cut-off wavelength in the UV-visible spectrum of less than or equal to about 420 nanometers.

11. The composition of claim 1, further comprising a polymer.

12. The composition of claim 11, wherein said polymer is a thermoplastic polymer selected from the group consisting of polyvinyl chloride, polyolefins, chlorinated polyolefins, polyethylene terephthalate, polybutylene terephthalate, polycyclohexylmethylene terephthalate, polyamides, polysulfones, hydrogenated polysulfones, polyimides, polyetherimides, polyethersulfones, polyphenylene sulfides, polyether ketones, polyether ether ketones, ABS resins, polystyrenes, hydrogenated polystyrenes, poly(cyclohexylethylene), poly(styrene-co-acrylonitrile), poly(styrene-co-maleic anhydride) polybutadiene, poly(methylmethacrylate), poly(methylmethacrylate-co-imide)copolymers, polyacrylonitrile, polyacetals, polycarbonates, polyphenylene, polyarylene ethers, polyamideimide, poly(ethylene-co-vinyl acetate), polyvinyl acetate, liquid crystal polymers, ethylene-tetrafluoroethylene copolymers, polyarylates, polyvinyl fluoride, polyvinylidene fluoride, polyvinylidene chloride, polytetrafluoroethylenes, epoxy resins, phenolic resins, alkyds, polyurethane, mineral filled silicone resins, bis-maleimide resins, cyanate ester resins, vinyl resins, and benzocyclobutene resins; and blends, mixtures and copolymers, reaction products, and composites comprising the foregoing polymers.

13. The composition of claim 11, wherein said at least one [benzo[4,5]imidazo(heterocycle)] compound has an absorption cut-off wavelength in the UV-visible spectrum of less than or equal to about 420 nanometers.

14. The composition of claim 13, comprising from about 0.001 parts per million to about 20 weight percent of said [benzo[4,5]imidazo(heterocycle)] compound, relative to an overall weight of said composition.

15. A compound having a structure I:

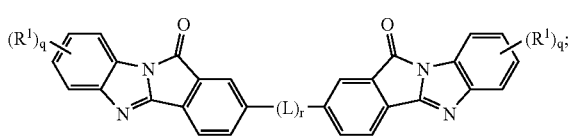

I wherein $R^1$ is independently selected from the group consisting of a hydrogen atom, electron withdrawing group, aliphatic group, cycloaliphatic group, aromatic group, divalent 1,2-cycloalkylidene group, or combinations thereof; "q" is an integer from 1–4, L is a linking group, and "r" is 0 or 1; and when "r" is 1, "L" is in dependently selected from the group consisting of S, O, $SO_2$, $CR^3R^4$, wherein $R^3$ and $R^4$ are independently selected from the group consisting of an aliphatic group, an aromatic group, a cycloaliphatic group, and combinations thereof.

16. The compound of claim 15, wherein "q"=1.

17. The compound of claim 16, wherein "L" is independently selected from the group consisting of S, O, $SO_2$, $CR^3R^4$, wherein $R^3$ and $R^4$ are independently selected from the group consisting of an aliphatic group, an aromatic group, a cycloaliphatic group, and combinations thereof and "r" is 1.

18. The compound of claim 17, wherein "r" is 0.

19. The compound of claim 18, wherein $R^1$ is independently selected from the group consisting of an ester group, a carboxylic acid group, a ketone group, a halogen group, a nitro group, a cyano group, a trifluoromethyl group, a sulfone group, and combinations thereof.

20. The compound of claim 19, wherein said ketone group has a formula $COR^7$ wherein $R^7$ is selected from the group consisting of a $C_1$–$C_{12}$ aliphatic, cycloaliphatic, or aromatic group.

21. The compound of claim 20, wherein $R^7$ is a phenyl group.

22. The compound of claim 19, wherein said ester group has a formula $COOR^8$, wherein $R^8$ is selected from the group consisting of a $C_1$–$C_{12}$ aliphatic, cycloaliphatic, or aromatic group.

23. The compound of claim 15, having an absorption cut-off wavelength in the UV-visible spectrum of less than or equal to about 420 nanometers.

24. A composition comprising the compound of claim 15 and further comprising a polymer.

25. The compound of claim 24, having an absorption cut-off wavelength in the UV-visible spectrum of less than or equal to about 420 nanometers.

26. The compound of claim 24, which exhibits a maximum fluorescence emission wavelength of greater than or equal to about 470 nanometers; and a Stokes shift of greater than or equal to about 80 nanometers.

27. A method for preparing a [2,2']bis{[benzo[4,5]imidazo[2,1-a]isoindolyl]-11-one} compound, said method comprising:
contacting an aromatic dianhydride having a structure III:

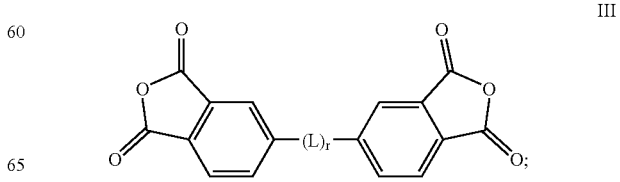

III wherein L is a linking group, and "r" is 0 or 1; with an aromatic diamine having a structure IV:

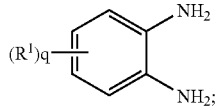

wherein $R^1$ is selected from the group consisting of a hydrogen atom, electron withdrawing group, organic group, divalent 1,2-cycloalkylidene group, or combinations thereof; and "q" is an integer from 0–4; and forming said [2,2']bis{[benzo[4,5]imidazo[2,1-a]isoindolyl]-11-one} compound having a structure I:

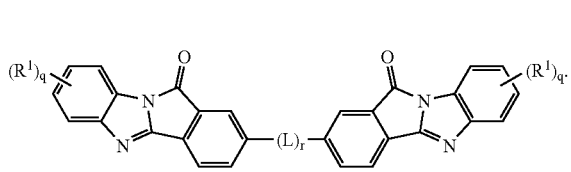

28. The method of claim 27, wherein said diamine is selected from the group consisting of ortho-phenylenediamine, 4-methoxycarbonyl-ortho-phenylenediamine, 4-acetyl-ortho-phenylenediamine, 4-methylsulfonyl-ortho-phenylenediamine, and mixtures thereof.

29. The method of claim 27, wherein "r" is 0, "q" is 1, and $R^3$ is a benzoyl group.

30. The method of claim 27, wherein said contacting comprises heating the aromatic dianhydride and the aromatic diamine in a solvent, said solvent being selected from the group consisting of an aliphatic carboxylic acid, an aromatic monohydroxy compound, a cycloaliphatic alcohol, halogenated and non-halogenated liquid aromatic hydrocarbons, N,N-dialkylamides, cyclic N-alkyl amides, and mixtures of the foregoing solvents.

31. The method of claim 27, further comprising a purification of said [2,2']bis{[benzo[4,5]imidazo[2,1-a]isoindolyl]-11-one}.

32. The method of claim 31, wherein said purification comprises:
treating [2,2']bis{[benzo[4,5]imidazo[2,1-a]isoindolyl]-11-one} with a first solvent,
isolating an intermediate [2,2']bi[benzo[4,5]imidazo[2,1-a]isoindolyl]-11,11'-dione,
treating said intermediate purified [2,2']bi[benzo[4,5]imidazo[2,1-a]isoindolyl]-11,11'-dione with a second solvent, and
isolating a purified [2,2']bi[benzo[4,5]imidazo[2,1-a]isoindolyl]-11,11'-dione.

33. The method of claim 32, wherein said first solvent and said second solvent comprises at least one member selected from the group consisting of an aromatic hydrocarbon and a partially hydrogenated aromatic hydrocarbon.

34. The method of claim 33, wherein said first solvent is dihydronaphthalene.

35. The method of claim 33, wherein said second solvent is selected from the group consisting of toluene, xylenes, mesitylene, and mixtures thereof.

36. A method for preparing a [7,7']bis{[benzo[4,5]imidazo[2,1-a]isoindolyl]-11-one} compound, the method comprising:
contacting an aromatic tetraamine having a structure V:

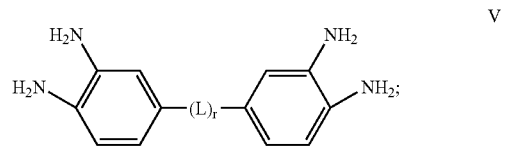

wherein "L" is a linking group, and 'r' is 0 or 1; with an aromatic monoanhydride having a structure VI:

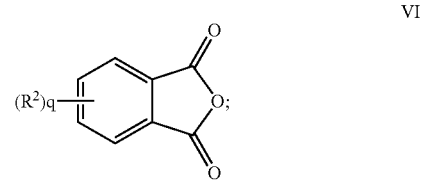

wherein $R^2$ selected from the group consisting of a hydrogen atom, electron withdrawing group, organic group, divalent 1,2-cycloalkylidene group, or combinations thereof and "q" is an integer from 0–4;
forming a first intermediate product;
treating said first intermediate product with a first solvent,
isolating a second intermediate product,
treating said intermediate product with a second solvent, and
isolating said [7,7']bi[benzo[4,5]imidazo[2,1-a]isoindolyl]-11,11'-dione compound having a structure II:

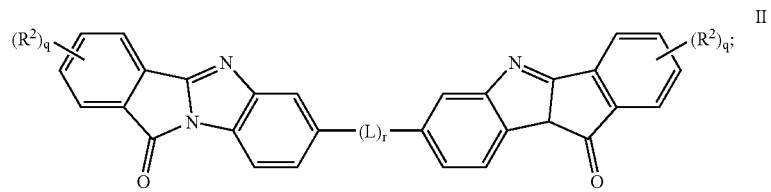

wherein said compound upon exposure to an excitation radiation having a wavelength of from about 330 nanometers to about 390 nanometers exhibits a fluorescence emission having a wavelength of from about 470 nanometers to less than 530 nanometers, and wherein the wavelengths are measured in bisphenol A polycarbonate matrix; said compound being present in a concentration sufficient to produce a composition capable of exhibiting said fluorescence emission.

37. The method of claim 36, wherein said [7,7']bis{[benzo[4,5]imidazo[2,1-a]isoindolyl]-11-one} compound has a 10 percent weight loss decomposition temperature, as measured in air of about 280° C. to about 420° C.

38. The method of claim 37, wherein said [7,7']bis{[benzo[4,5]imidazo[2,1-a]isoindolyl]-11-one} compound further exhibits a Stokes shift of about 80 nanometers to about 180 nanometers.

* * * * *